United States Patent [19]
Nelson

[11] Patent Number: 5,432,305
[45] Date of Patent: Jul. 11, 1995

[54] PENETROMETER ACOUSTIC SOIL SENSOR

[75] Inventor: George F. Nelson, Coon Rapids, Minn.

[73] Assignee: Unisys Corporation, St. Paul, Minn.

[21] Appl. No.: 279,411

[22] Filed: Jul. 25, 1994

[51] Int. Cl.6 .......................... G01V 1/00; G01N 3/32
[52] U.S. Cl. ........................................ 181/101; 73/84; 73/594
[58] Field of Search .................. 367/14; 181/101, 106, 181/122, 401; 73/84, 594, 152; 175/50

[56] References Cited

U.S. PATENT DOCUMENTS

| | | | |
|---|---|---|---|
| 3,690,166 | 9/1972 | Grice | 73/152 |
| 3,859,598 | 1/1975 | McElwain et al. | 181/101 |
| 4,382,384 | 5/1983 | Mitchell et al. | 73/84 |
| 4,383,591 | 5/1983 | Ogura | 181/106 |
| 4,492,111 | 1/1985 | Kirkland | 73/84 |
| 4,805,725 | 2/1989 | Paulsson | 181/106 |
| 5,177,709 | 1/1993 | Baziw | 367/38 |

Primary Examiner—Ian J. Lobo
Attorney, Agent, or Firm—Glenn W. Bowen

[57] ABSTRACT

A acoustic-penetrometer probe and method for determining the presence of materials in a region proximate the penetrometer probe through measurement of reflected acoustic waves, with the probe having a driving head on one end to permit forcing the driving head into the soil, with the probe including an acoustic generator mounted in the probe for generating a below-ground acoustic wave that normally travels away from the acoustic generator, and an acoustic detector located in the probe to measure acoustic waves reflected from objects or materials located proximate the probe to thereby provide a user with information on the presence of materials proximate a radial region located around the probe.

17 Claims, 4 Drawing Sheets

PENETROMETER ACOUSTIC SOIL SENSOR

FIELD OF THE INVENTION

This invention relates to apparatus for analysis of subsoil and, more specifically, to an acoustic cone penetrometer probe that includes both an acoustic wave generator for generating an acoustic wave and an acoustic detector for receiving acoustic waves reflected from underground materials located in the region surrounding the probe.

BACKGROUND OF THE INVENTION

The concept of using acoustic or seismic waves to determine materials in the soil is old in the art. Typically, an explosion or sudden impact generates an acoustic wave on the surface of the soil and belowground acoustic detectors measure the received acoustic signals at two or more locations. By measuring the difference in arrival times of the acoustic signal, one determines the average velocities through the soft. If the velocity differs from the expected velocity, the operator is alerted to the fact that the soft lacks homogeneity and can contain objects or contaminates. In contrast, the present invention measures the strength of reflected waves and includes a probe for driving into the soil, with the probe having an acoustic generator and sound detectors to provide an "on-the-go" measurement of materials in the region proximate the probe.

In the present invention, an acoustic generator and multiple acoustic receivers are placed within a cone penetrometer probe to locate objects, soil contaminates and changes in strata where it is likely that pools of soil contaminates may be present.

One object of this invention is to determine the homogeneity or lack of homogeneity of the subsurface soil matrix in a region of approximately 10 meters surrounding the probe. It is known that the measurements performed by various cone-probe sensors is representative of the soil in contact or within a few centimeters of the probe. With such probes the information obtained is meaningful for soils that contact the probe or are extremely close to the probe. However, the information is not necessarily meaningful for all the soil within a few meters of the probe. For example, Dense Non-aqueous Phase Liquids (DNAPL) can permeate the soil in a ganglia structure resulting in filaments of contaminates only a few centimeters thick that extend over a large region. With probes that determine only the soil contaminants contacting the probe or extremely close to the probe, it is possible to miss such soil contaminates unless the probe actually contacts the soil contaminates. For example, Laser Induced Fluorescence produces a measurement of hydrocarbon contamination for a thin strip of soil adjacent to the probe as the probe is being pushed into the soil. In contrast, the present invention detects soil contaminates and changes in strata in regions within approximately 10 meters of the probe. The present invention measures reflected waves to determine changes in time and changes in amplitude of a wave resulting from the presence of materials of different densities in the soil.

Thus the present invention can determine the homogeneity of the surrounding soil in a larger region around the probe as opposed to devices which can only measure soil contaminates in contact with or extremely close to the probe.

In addition to directly locating soil contaminates, the present invention indirectly locates soil contaminates by detecting significant changes in strata, such as fractures and cavities, which are likely to contain underground pools of contaminates. By identifying soil regions likely to contain pools of contaminates, the operator obtains information on ideal placement of the probe to check for the presence of underground pools of contaminates. With the capability to identify underground regions that are likely to contain pools of contaminates, the present invention improves the ability to map a site for contamination more fully and also to potentially decrease the cost of site mapping because the operator knows where to place the probe to look for contaminates.

The operation of the present invention is based upon measurements of the change in reflection of energy of a wave due to the discontinuities in the index of refraction of different underground materials. The discontinuities in the index of refraction result in a change in the velocity of propagation of sound, thereby providing information on the subsurface geology in the region around the probe.

BRIEF DESCRIPTION OF THE PRIOR ART

U.S. Pat. No. 5,177,709 shows a method and apparatus for determining the directional velocity of acoustic waves by using a seismic sensor on a cone penetrometer located below ground to measure directly the waves generated by a seismic event at ground level. Apparatus are included for obtaining a more accurate signal.

U.S. Pat. No. 4,382,384 shows a subsoil penetrometer probe which directly measures the acoustical sound produced by the friction of the soil particles as they slide past the penetrometer. That is, as the soil grains slide and roll over each other as the cone penetrometer moves through the soil, the soil grains generate noise which is measured by a microphone located in the probe. The signal depends on the probe moving through the soil to obtain a useful signal and the measurements are only measurable in the soil in direct contact with or extremely close to the probe.

SUMMARY OF THE INVENTION

Briefly, the invention comprises an acoustic-penetrometer probe having both a sound generator and an acoustic detector for measuring wave strength and the time for a reflected wave to arrive at the probe, and a method for determining the presence of materials in a region proximate the penetrometer probe with the probe. The probe has a driving head on one end to permit forcing the driving head into the soil with the probe including an acoustic generator mounted internally for generating a below-ground acoustic wave that normally travels away from the acoustic generator and an acoustic detector located in the probe to measure acoustic waves reflected from objects or materials located proximate the probe to thereby provide a user with information on the presence of materials within a radius of a few meters around the probe.

DESCRIPTION OF THE PREFERRED EMBODIMENT

Figure 1:
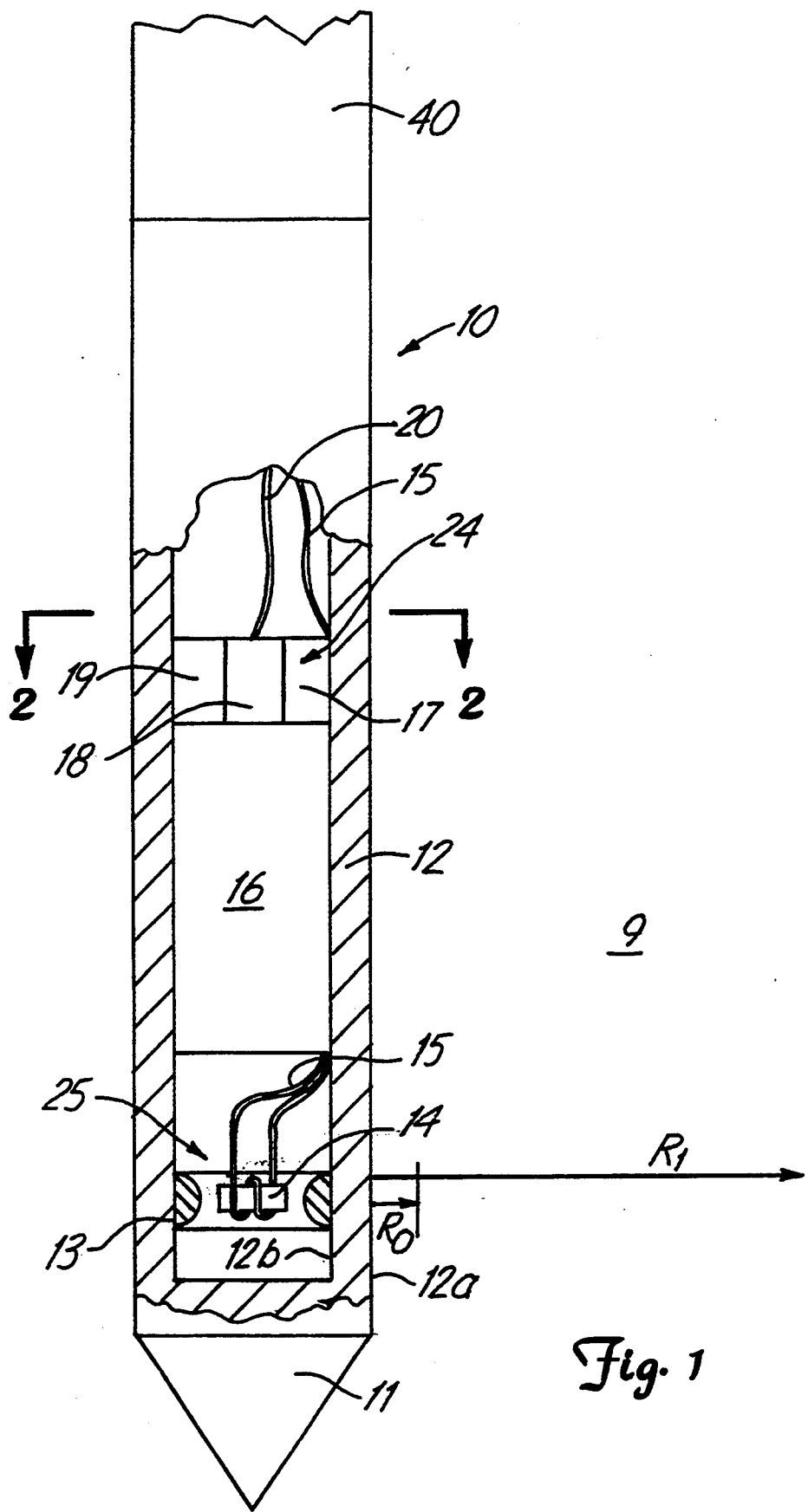
FIG. 1 is a partial sectional view of the probe of the present invention.

FIG. 1 reference numeral 10 generally identifies a cylindrical acoustic-penetrometer probe of the present invention which is connected to a cylindrical housing 40 through means such as male and female threads. The lower portion of probe 10 is cut away to reveal an acoustic generator or impulse-generating device 25 located inside probe 10 and an acoustic or sound-detecting device 24 also located inside probe 10. Reference numeral 11 identifies a cone-shaped driving head on the probe for penetrating the soil.

Figure 3:
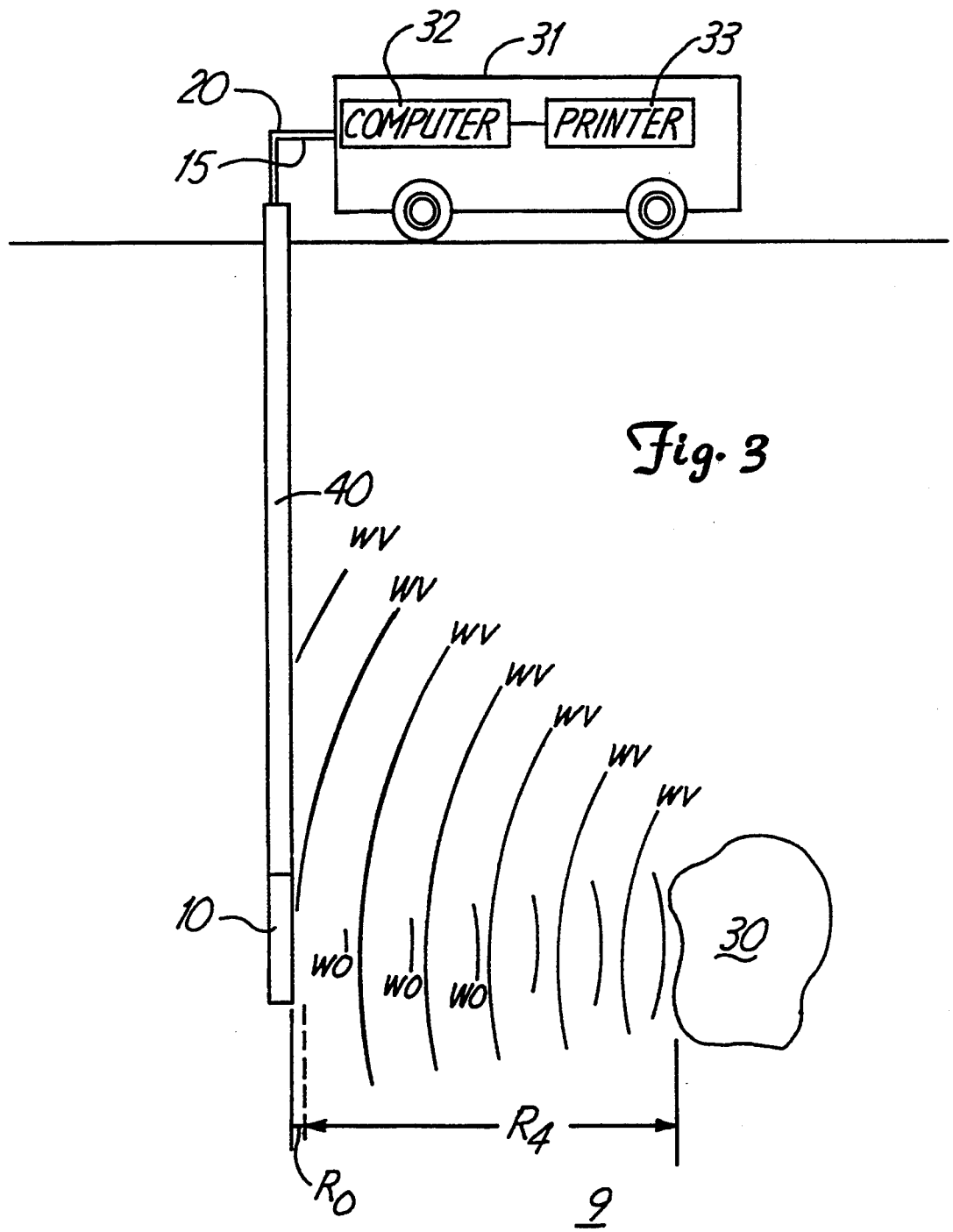
FIG. 3 is a partial schematic view showing the system for measuring the materials present in the soil.

The penetrometer probe 10 comprises a cylindrical pipe 12 made of steel or the like which carries therein an impulse generator 25. Impulse generator 25 comprises an electromagnet striker 14 which is intermittently powered through electrical wires 15 connected to a control center having a computer 32 and printer 33 in an above-ground vehicle 31 (FIG. 3). Located around the interior of pipe 12 is an annular metal ring 13 which is held in engagement with the inside surface 12c of pipe 12 through a compression fit. The purpose of metal ring 13 is to create sufficient mass at the point of impact of striker 14 to radially and uniformly distribute the energy of the impulse generated by the action of electromagnet striker 14 outward from probe 10. If desired, metal ring 13 could be made integral with the probe.

In operation of the sound generator 25, the impulse generated by applying an electrical signal to wires 15 causes striker 14 of the solenoid 25 to hit ring 13 which distributes the impulse in a 360-degree circle around the inside of the probe. The impulse passes through the walls of the probe to generate an acoustic wave which emanates radially outward through the soil.

Figure 2:
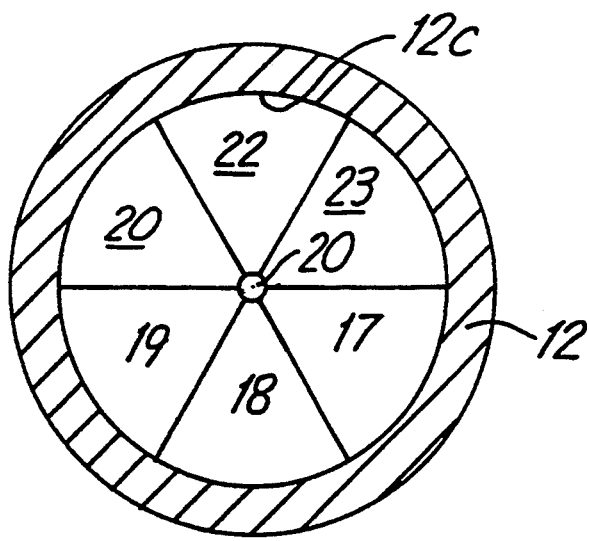
FIG. 2 is a cross-sectional view taken along lines 2—2 of FIG. 1.

Located above impulse generator 25 is a sound-deadening or insulation material 16 to acoustically isolate the sound generator from the sound detector. Located above the sound-deadening material 16 is the acoustic detector 24 having a set of six circumferentially spaced microphones or geophones 17, 18, 19, 21, 22, and 23, which are shown in FIG. 2. FIG. 2 also shows the geophones are circumferentially spaced 360 degree around the interior of surface 12c of pipe 12. Electrical lead 20 for the acoustic detectors extends up to the control center in the above-ground vehicle 31. In the preferred operation of the acoustic detector, the acoustic detector is shut off at the moment of impact of striker 14 and, for an acoustic wave propagation time of a few centimeters, to avoid measuring a direct wave at sound detectors 24.

FIG. 3 schematically illustrates the operation of the invention as the impulse generator in probe 10 generates an acoustical wave $w_o$. Traveling outward, wave $w_o$ encounters an obstacle 30 which reflects a wave $w_r$ backwards which is then received by geophones 17, 18, 19, 21, 22 and 23 which are located in probe 10.

Figure 4:
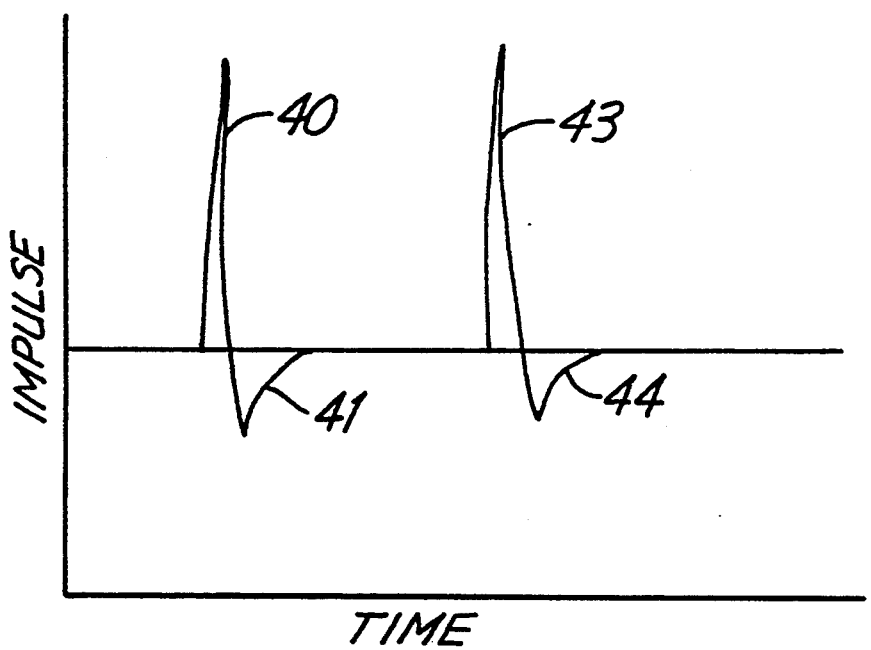
FIG. 4 shows the type of impulse generated with the embodiment of FIG. 1.

FIG. 4 illustrates the typical type of impulse generated by solenoid 25 of the present invention. The waveform has a sharp spike 40 with a rapidly decaying signal 41 that is naturally damped by pipe 12 and surrounding soil 9. At predetermined intervals the impulse generator repeats the impulse as indicated by spike 43 with a similar corresponding decay 44.

Figure 5:
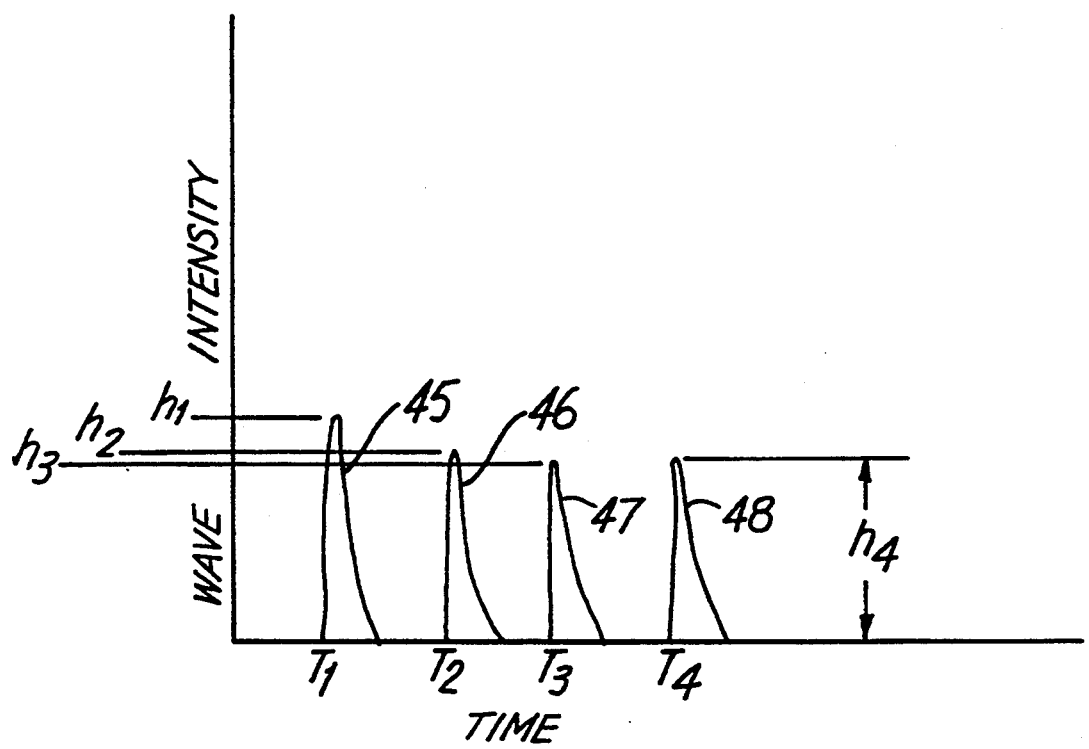
FIG. 5 shows the reflective waves received by the sensing device.

FIG. 5 indicates the type of signal obtainable from reflected waves $w_r$. That is, a reflective wave $w_r$ from an object located radially outward the probe is received at different times at microphones 17, 18, 19, 21, 22 and 23 since the microphones are spaced peripherally around the inner surface 12c of probe. That is, a first portion of reflected wave $w_r$ 45 is received at a first microphone at time $t_1$, a second portion of reflected wave $w_r$ 46 is received at a second microphone at time $t_2$, a third portion of reflected wave $w_r$ 47 is received at a third microphone at time $t_3$ and a fourth portion of reflected wave $w_r$ 48 is received at a fourth microphone at time $t_4$. If the sound wave reflects off an object located on only one side of the probe, the reflected signal may be so low that the microphones located behind and on the side of the probe opposite the object may not detect the object at all because the probe is cylindrical. It will also be noted that the invention takes advantage of the damping effect of the soil so that the acoustic signals below a certain level do not produce reflected waves that are strong enough to be detected by the microphones in the probe. That is, the portion of the signal 41 and 44 do not appear in the received signal as the sound detectors 25 are selected such that the reflected signals of unwanted portions of the signal are normally not measurable.

FIG. 5 also shows the amplitude of the wave $w_r$ at the various positions as indicated by h1, h2 h3 and h4. The information regarding the attenuation of the signal coupled with the times of arrival of the signal at the individual microphones can be used to geometrically locate the distance of the object from the probe as well as the angular position of the object with respect to the probe.

It should be pointed out that the acoustic waveform emanates radially downward from the probe so the probe can also detect objects located in front of its path. Thus the probe alerts a user to a condition that might break it if the probe hits an object in front of it. If desired the probe could have an exterior surface that was at an obtuse angle from the vertical to direct the acoustic signals in a generally downward direction rather than laterally outward. This would allow for increased capability of determining materials in front of the probe as the probe is driven into the ground.

In operation of the present invention as indicated in FIG. 3, a sound wave $w_o$ is generated in the lower area of penetrometer probe 10 and travels radially outward, away from the exterior of penetrometer 10. The penetrometer measures reflected signals from objects within a first range indicated by $R_0$, a second range indicated by $R_1$. Typically, with an electrical solenoid to supply an impact, the sensing range extends a distance $R_0$ which may be several centimeters to distance $R_1$ which is a few meters. The use of larger impacts or different types of signals can extend or shorten the working range of the probe. Thus the present invention provides "on the go" measurement of objects in the soil that are proximate the probe by use of both a sound generator and sound detector located in the probe. That is, the continuous operation of this sensor while the probe is being pushed into the soil, provides a horizontal radial picture of the discontinuities in the soil.

I claim:

1. A acoustic-penetrometer probe for determining the presence of materials in a region proximate the penetrometer probe comprising:

a housing having a first end and a second end;

a probe connected to said housing;

a driving head on said probe to permit forcing of the housing and driving head into the soil;

an acoustic generator mounted in said probe for generating a below-ground acoustic wave that normally travels away from the acoustic generator, the acoustic generator being operable to generate waves at the same time as the probe is forced into the soil for simultaneous wave generation and probing such that an on-the-go-measurement of waves is provided; and an acoustic detector located in said probe to measure acoustic waves reflected from objects or a material located proximate the housing to thereby provide a user with information on the presence of materials proximate the region around the probe.

2. The probe of claim 1 including an above-ground computer for receiving the information and comparing the information to a reference signal to provide an operator with information on the materials and objects located proximate the probe.

3. The probe of claim 1 wherein the acoustic generator comprises an electrical solenoid having a striker for impacting said probe when an electrical signal is applied to said solenoid.

4. The probe of claim 3 including an annular member circumferentially spaced around the inside of said probe to provide acoustic waves that emanate in a 360 circle outward from the probe.

5. The probe of claim 1 wherein the probe includes a plurality of acoustic detectors circumferentially spaced around said probe to measure the arrival time of a reflected acoustic wave at each of the plurality of acoustic detectors.

6. The probe of claim 1 wherein a sound insulation member is located in said probe between the acoustic generator and the sound detector for isolating an unreflected sound wave within the probe from the acoustic detector.

7. The probe of claim 1 including member for deactivating the sound detector until the sound wave is at least two centimeters from the probe.

8. The probe of claim 1 wherein the probe is cylindrical and contains at least six acoustic sound detectors.

9. The probe of claim 1 wherein the sound detector comprises a geophone contacting an inside surface of the probe to receive sounds through a sidewall of the probe.

10. The probe of claim 1 wherein the acoustic detector and the sound connect to an above ground computer for determining the nature of the material in the soil around the probe.

11. The method of determining the presence of materials proximate a probe located in subsoil comprising the steps of:

generating an underground acoustic wave from inside a probe forceable into the soil to direct the acoustic wave radially outward from the probe, the wave being generated at the same time as the probe is being forced into the soil;

measuring the time for the acoustic wave to be reflected to an underground sound detector located in the probe; and comparing the measured time for the acoustic wave to be reflected from the underground sound detector to a reference signal to determine the presence of material located in the subsoil.

12. The method of claim 11 including measuring the time for the acoustic wave to be reflected to at least two different locations to determine the relative position of an object from the probe.

13. The method of claim 12 including measuring the amplitude of a reflected acoustic wave and comparing it to the amplitude of the generated acoustic wave to determine the attenuation of the reflected wave.

14. The method of claim 13 including the step of comparing the attenuation of the reflected wave to a reference signal to determine the type and presence of materials present in the subsoil.

15. The method of claim 11 including generating the acoustic wave to a radius of no more than about 10 meters.

16. An acoustic-penetrometer probe for determining the presence of materials in a region proximate the penetrometer probe comprising:

a housing having a first end and a second end;

a probe connected to said housing;

a driving head on one said probe to permit forcing of the housing and driving head into the soil;

an acoustic generator mounted in said probe for generating a below-ground acoustic wave that normally travels away from the acoustic generator, the acoustic generator comprising an electrical solenoid having a striker and annular member in the probe for being struck by the striker when an electrical solenoid is applied to the solenoid, the annular member circumferentially spaced around the inside of the probe to provide acoustic waves that emanate in a 360 circle outward from the probe and to uniformly distribute the energy of the impulse generated by the action of the striker;

a plurality of acoustic detectors located in said probe to measure acoustic waves reflected from objects or a material located proximate the housing to thereby provide a user with information on the presence and angular position of materials proximate the region around the probe, the detectors being circumferentially spaced around the probe to measure an arrival time of a reflected wave at each of the plurality of acoustic detectors, the detectors being deactivated until the sound wave is at least two centimeters from the probe; and a sound insulation member located in the probe between the acoustic generator and the sound detector for isolating an unreflected sound wave within the probe from the acoustic detector.

17. The acoustic-penetrometer probe of claim 16 wherein the annular member being metal and being on an inside wall of the probe and being concentric with the cylindrical probe; and a plurality of at least six acoustic detectors located in said probe to measure amplitude and elapsed time of an acoustic wave reflected from materials located proximate the housing to thereby provide a user with information on both the presence and angular location of materials proximate the region around the probe.

* * * * *